United States Patent
Gloegaard et al.

(10) Patent No.: US 8,273,874 B2
(45) Date of Patent: Sep. 25, 2012

(54) METHOD OF DYNAMIC NUCLEAR POLARISATION (DNP) AND COMPOUNDS AND COMPOSITIONS FOR USE IN THE METHOD

(75) Inventors: Christian Gloegaard, Oslo (NO); Rolf Servin, Malmo (SE); Mikkel Thaning, Tygelsjo (SE)

(73) Assignee: GE Healthcare AS, Oslo (NO)

( * ) Notice: Subject to any disclaimer, the term of this patent is extended or adjusted under 35 U.S.C. 154(b) by 711 days.

(21) Appl. No.: 12/376,810

(22) PCT Filed: Aug. 29, 2007

(86) PCT No.: PCT/NO2007/000307
§ 371 (c)(1),
(2), (4) Date: Feb. 9, 2009

(87) PCT Pub. No.: WO2008/026937
PCT Pub. Date: Mar. 6, 2008

(65) Prior Publication Data
US 2010/0190967 A1    Jul. 29, 2010

(30) Foreign Application Priority Data
Aug. 30, 2006   (NO) .................................. 20063873

(51) Int. Cl.
*A61B 5/00* (2006.01)
*C07B 47/00* (2006.01)

(52) U.S. Cl. ..................... 540/145; 424/9.362; 424/9.61
(58) Field of Classification Search ................. 540/145; 424/9.362, 9.61
See application file for complete search history.

(56) References Cited

FOREIGN PATENT DOCUMENTS
WO   2006/054903   5/2006
WO   2007/064226   6/2007

OTHER PUBLICATIONS

Broan et al., J'nal of Chem. Soc., PT., No. 1 (1991) pp. 87-99.*
Broan, C.J. et.al. "Structure and solution of indium and gallium complexes of 1,4,7-triazacyclononanetriacetate and of yttrium complexes of 1,4,7,10-tetraazacyclododecanetetraacetate and related ligands: kinetically stable complexes for using in imaging and radioimmunotherapy. X-ray molecular structure of the indium and" Journal of the Chemical Society, Perkin Transactions 2, Chemical Society, Letchworth, GB, No. 1, 1991, pp. 87-99.
Liu, S, et.al. "Comparison of yttrium and indium complexes of dota-ba and dota-mba: models for 90Y and 111IN-labeled dota-biomolecule conjugates" Bioconjugate chemistry, ACS, Washington, DC, vol. 13, No. 4, Jul. 2002, pp. 902-913.
PCT/NO2007/000307 Int'l Search Report/Written Opinion dated Aug. 2007.

* cited by examiner

*Primary Examiner* — Paul V. Ward
(74) *Attorney, Agent, or Firm* — Jean K. Testa

(57) ABSTRACT

The invention relates to an improved method of dynamic nuclear polarisation (DNP) of carboxylic acids and to compounds and compositions for use in the method.

19 Claims, No Drawings

METHOD OF DYNAMIC NUCLEAR POLARISATION (DNP) AND COMPOUNDS AND COMPOSITIONS FOR USE IN THE METHOD

This application is a filing under 35 U.S.C. 371 of international application number PCT/NO2007/000307, filed Aug. 29, 2007, which claims priority to application number 20063873 filed Aug. 30, 2006, in Norway the entire disclosure of which is hereby incorporated by reference.

The invention relates to an improved method of dynamic nuclear polarisation (DNP) of carboxylic acids and to compounds and compositions for use in the method.

Magnetic resonance (MR) imaging (MRI) is a imaging technique that has become particularly attractive to physicians as it allows for obtaining images of a patients body or parts thereof in a non-invasive way and without exposing the patient and the medical personnel to potentially harmful radiation such as X-rays. Because of its high quality images, MRI is a favourable imaging technique of soft tissue and organs and it allows for the discrimination between normal and diseased tissue, for instance tumours and lesions.

MRI may be carried out with or without MR contrast agents. However, contrast-enhanced MRI usually enables the detection of much smaller tissue changes which makes it a powerful tool for the detection of early stage tissue changes like for instance small tumours or metastases.

Several types of contrast agents have been used in MRI. Water-soluble paramagnetic metal chelates, for instance gadolinium chelates like Omniscan™ (GE Healthcare) are widely used MR contrast agents. Because of their low molecular weight they rapidly distribute into the extracellular space (i.e. the blood and the interstitium) if administered into the vasculature. They are also cleared relatively rapidly from the body.

Blood pool MR contrast agents on the other hand, for instance superparamagnetic iron oxide particles, are retained within the vasculature for a prolonged time. They have proven to be extremely useful to enhance contrast in the liver but also to detect capillary permeability abnormalities, e.g. "leaky" capillary walls in tumours for example as a result of angiogenesis.

Despite the undisputed excellent properties of the aforementioned contrast agents their use is not without any risks. Although paramagnetic metal chelate complexes have usually high stability constants, it is possible that toxic metal ions are released in the body after administration. Further, these type of contrast agents show poor specificity.

Another class of MR imaging agents are hyperpolarised MR imaging agents. WO-A-99/35508 discloses a method of MR investigation of a patient using a solution of a hyperpolarised high $T_1$ agent as MRI imaging agent. The term "hyperpolarisation" means enhancing the nuclear polarisation of NMR active nuclei present in the high $T_1$ agent, i.e. nuclei with non-zero nuclear spin, preferably $^{13}C$- or $^{15}N$-nuclei. Upon enhancing the nuclear polarisation of NMR active nuclei, the population difference between excited and ground nuclear spin states of these nuclei is significantly increased and thereby the MR signal intensity is amplified by a factor of hundred and more. When using a hyperpolarised $^{13}C$- and/or $^{15}N$-enriched high $T_1$ agent, there will be essentially no interference from background signals as the natural abundance of $^{13}C$ and/or $^{15}N$ is negligible and thus the image contrast will be advantageously high. The main difference between conventional MRI contrast agents and these hyperpolarised high $T_1$ agents is that in the former changes in contrast are caused by affecting the relaxation times of water protons in the body whereas the latter class of agents can be regarded as non-radioactive tracers, as the signal obtained arises solely from the agent.

A variety of possible high $T_1$ agents for use as MR imaging agents are disclosed in WO-A-99/35508, including non-endogenous and endogenous compounds like acetate, pyruvate, oxalate or gluconate, sugars like glucose or fructose, urea, amides, amino acids like glutamate, glycine, cysteine or aspartate, nucleotides, vitamins like ascorbic acid, penicillin derivates and sulfonamides. It is further stated that intermediates in metabolic cycles such as the citric acid cycle like fumaric acid and pyruvic acid are preferred imaging agents for MR imaging of metabolic activity.

Hyperpolarised MR imaging agents that play a role in the metabolic processes in the human and non-human animal body are of great interest, as these hyperpolarised imaging agents can be used to get information about the metabolic state of a tissue in an in vivo MR investigation, i.e. they are useful for in vivo imaging of metabolic activity. Information of the metabolic status of a tissue might for instance be used to discriminate between healthy and diseased tissue.

Pyruvate is a compound that plays a role in the citric acid cycle and the conversion of hyperpolarised $^{13}C$-pyruvate to hyperpolarised metabolites can be used for in vivo MR study of metabolic processes in the human body. Hyperpolarised $^{13}C$-pyruvate may for instance be used as an MR imaging agent for in vivo tumour imaging as described in detail in WO-A-2006/011810 and WO-A-2006/011809 and for assessing the viability of myocardial tissue by MR imaging as described in detail in WO-A-2006/054903.

Pyruvate is an endogenous compound which is very well tolerated by the human body, even in high concentrations. As a precursor in the citric acid cycle, pyruvate plays an important metabolic role in the human body. Pyruvate is converted into different compounds: its transamination results in alanine, via oxidative decarboxylation, pyruvate is converted into acetyl-CoA and carbon dioxide (which is further converted to bicarbonate), the reduction of pyruvate results in lactate and its carboxylation in oxaloacetate.

Further, the metabolic conversion of hyperpolarised $^{13}C$-pyruvate to its metabolites hyperpolarised $^{13}C$-lactate, hyperpolarised $^{13}C$-bicarbonate (in the case of $^{13}C_1$-pyruvate, $^{13}C_{1,2}$-pyruvate or $^{13}C_{1,2,3}$-pyruvate only) and hyperpolarised $^{13}C$-alanine can be used for in vivo MR study of metabolic processes in the human body. $^{13}C_1$-pyruvate has a $T_1$ relaxation in human full blood at 37° C. of about 42 s, however, the conversion of hyperpolarised $^{13}C$-pyruvate to hyperpolarised $^{13}C$-lactate, hyperpolarised $^{13}C$-bicarbonate and hyperpolarised $^{13}C$-alanine has been found to be fast enough to allow signal detection from the $^{13}C$-pyruvate parent compound and its metabolites. The amount of alanine, bicarbonate and lactate is dependent on the metabolic status of the tissue under investigation. The MR signal intensity of hyperpolarised $^{13}C$-lactate, hyperpolarised $^{13}C$-bicarbonate and hyperpolarised $^{13}C$-alanine is related to the amount of these compounds and the degree of polarisation left at the time of detection, hence by monitoring the conversion of hyperpolarised $^{13}C$-pyruvate to hyperpolarised $^{13}C$-lactate, hyperpolarised $^{13}C$-bicarbonate and hyperpolarised $^{13}C$-alanine it is possible to study metabolic processes in vivo in the human or non-human animal body by using non-invasive MR imaging or MR spectroscopy.

The MR signal amplitudes arising from the different pyruvate metabolites vary depending on the tissue type. The unique metabolic peak pattern formed by alanine, lactate, bicarbonate and pyruvate can be used as fingerprint for the metabolic state of the tissue under examination.

It has to be stressed that the signal of a hyperpolarised imaging agent decays due to relaxation and—upon administration to the patient's body—dilution. Hence the $T_1$ value of the imaging agents in biological fluids (e.g. blood) must be sufficiently long (high) to enable the agent to be distributed to the target site in the patient's body in a highly hyperpolarised state. Apart from the imaging agent having a high $T_1$ value, it is extremely favourable to achieve a high polarisation level. If a hyperpolarised imaging agent has a high polarisation level, decay due to relaxation and dilution occurs with the same rate, however, by having a higher "starting level", the polarisation retained in the hyperpolarised imaging after a given time period is higher. The higher the polarisation level in the imaging agent the stronger the MR signals which can be detected from the imaging agent.

Several methods for obtaining hyperpolarised high $T_1$ agents are disclosed in WO-A-99/35508, one of them is the dynamic nuclear polarisation (DNP) technique whereby polarisation of a sample is effected by a polarising agent or so-called DNP agent, a compound comprising unpaired electrons. During the DNP process, energy, normally in the form of microwave radiation, is provided, which will initially excite the DNP agent. Upon decay to the ground state, there is a transfer of polarisation from the unpaired electron of DNP agent to the NMR active nuclei of the sample. Generally, a moderate or high magnetic field and a very low temperature are used in the DNP process, e.g. by carrying out the DNP process in liquid helium and a magnetic field of about 1 T or above. Alternatively, a moderate magnetic field and any temperature at which sufficient polarisation enhancement is achieved may be employed. The DNP technique is for example described in WO-A-98/58272 and in WO-A-01/96895, both of which are included by reference herein.

The DNP agent plays a decisive role in the DNP process as its choice has a major impact on the level of polarisation that can be achieved in the sample to be polarised. A variety of DNP agents—in WO-A-99/35508 denoted "OMRI contrast agents"—is known. The use of oxygen-based, sulfur-based or carbon-based stable trityl radicals as described in WO-A-99/35508, WO-A-88/10419, WO-A-90/00904, WO-A-91/12024, WO-A-93/02711 or WO-A-96/39367 has resulted in high levels of polarisation in a variety of different samples.

We have now surprisingly found that the addition of certain Gd-chelates to a composition comprising a trityl radical as DNP agent and pyruvic acid which is to be polarised by the DNP method results in a remarkably increased polarisation level in the pyruvic acid. This is especially favourable in a clinical situation where hyperpolarised pyruvate derived from dissolving solid hyperpolarised pyruvic acid obtained by DNP in a base-containing aqueous dissolution medium is used as an MR imaging agent in an MR examination procedure of a patient. If the polarisation level of pyruvic acid could be for instance enhanced by a factor x, theoretically only one $x^{th}$ of the concentration of pyruvate needs to be used in the MR examination procedure. This is of course advantageous not only from an economical perspective but also from a safety point of view since possible unwanted side effects due to high MR imaging agent concentrations and dose can be avoided.

Thus, viewed from a first aspect, the present invention provides a method of producing a solid hyperpolarised carboxylic acid said method comprising preparing a composition comprising the carboxylic acid, a trityl radical and a Gd-chelate of formula (1)

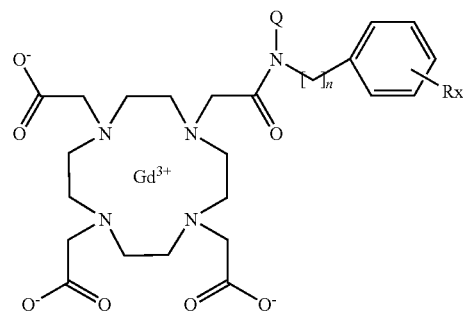

(1)

wherein
n is 1 to 10;
x is 0 to 3;
R is identical or different and represents fluoro, a straight chain or branched $C_1$-$C_6$-alkyl group, or an aromatic or non-aromatic cyclic group containing 5 to 10 carbon atoms; and
Q is H, a straight chain or branched $C_1$-$C_6$-alkyl group, or an aromatic or non-aromatic cyclic group containing 5 to 10 carbon atoms or

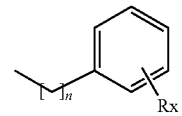

wherein n, x and R are as defined above;
and carrying out dynamic nuclear polarisation on the composition.

The terms "hyperpolarised" and "polarised" are used interchangeably hereinafter and denote a nuclear polarisation level in excess of 0.1%, more preferred in excess of 1% and most preferred in excess of 10%.

The level of polarisation may for instance be determined by solid state NMR measurements of the NMR active nucleus in the frozen hyperpolarised carboxylic acid. For instance, if the NMR active nucleus in the hyperpolarised carboxylic acid is $^{13}$C, a solid state $^{13}$C-NMR of said hyperpolarised carboxylic acid is acquired. The solid state $^{13}$C-NMR measurement preferably consists of a simple pulse-acquire NMR sequence using a low flip angle. The signal intensity of the hyperpolarised carboxylic acid in the NMR spectrum is compared with signal intensity of the carboxylic acid in a NMR spectrum acquired before the dynamic nuclear polarisation process. The level of polarisation is then calculated from the ratio of the signal intensities of before and after DNP.

In a similar way, the level of polarisation for dissolved hyperpolarised carboxylic acid may be determined by liquid state NMR measurements of the NMR active nucleus in the liquid hyperpolarised carboxylic acid. Again the signal intensity of the dissolved hyperpolarised carboxylic acid is compared with the signal intensity of the dissolved carboxylic acid before the dynamic nuclear polarisation process. The level of polarisation is then calculated from the ratio of the signal intensities before and after DNP.

The term "carboxylic acid" denotes a chemical entity which comprises at least one carboxyl group, i.e. COOH-group.

Although written in the singular form, the term "carboxylic acid" denotes a chemical entity or entities, i.e. a certain carboxylic acid or several different carboxylic acids, e.g. mixtures of several different carboxylic acids. As an example pyruvic acid is a certain carboxylic acid and the method according to the invention can be used to produce hyperpolarised pyruvic acid. Further, as an example pyruvic acid and lactic acid are several different carboxylic acids and the method of the invention can be used to produce a mixture of hyperpolarised pyruvic acid and hyperpolarised lactic acid.

The method according to the invention leads to high polarisation levels in the carboxylic acid to be polarised.

The carboxylic acid in the context of the present invention may be a monocarboxylic acid like for instance formic acid, acetic acid, lactic acid, pyruvic acid, nicotinic acid or fatty acids like palmitic acid or oleic acid. In another embodiment, the carboxylic acid may be a di-or polycarboxylic acid like for instance malic acid, fumaric acid, succinic acid, methylene succinic acid, malonic acid or citric acid or oxalic acid. Apart from comprising at least one carboxyl group, the carboxylic acid may contain further functional groups and/or heteroatoms. Preferred functional groups are amino groups and examples of carboxylic acids containing amino groups are amino acids like standard amino acids, preferably glycine, alanine, cysteine, glutamic acid, aspartic acid, glutamate, tryptophan and serine but also non-standard amino acids, preferably GABA (gamma-aminobutyric acid), homocysteine, sarcosine or the like. Other preferred functional groups that may be present in the carboxylic acid molecule are ketogroups—preferred examples of such compounds are pyruvic acid, oxaloacetic acid or α-ketoglutaric acid, or hydroxy groups—preferred examples of such compounds are lactic acid and salicylic acid. In another preferred embodiment, the carboxylic acid contains one or more heteroatoms, like for instance a nitrogen atom as in nicotinic acid.

Preferred carboxylic acids used in the method of the invention are drug candidates, more preferably small molecules e.g. less than 2000 Da, or a mixture of several drug candidates and the hyperpolarised drug candidate(s) obtained by the method of the invention may be used in NMR bioassays to for instance determine binding affinity to a certain receptor or in enzyme assays. Such assays are described in WO-A-2003/089656 or WO-A-2004/051300 and they are preferably based on the use of liquid state NMR spectroscopy which means that the composition containing the solid hyperpolarised drug candidate(s) has to be liquefied after polarisation, preferably by dissolving or melting it. The carboxylic acid may or may not be isotopically enriched.

In another preferred embodiment, the carboxylic acids used in the method of the invention are to be used as MR imaging agents. The term "MR imaging agent" denotes a compound which can be used as an MR imaging agent in MR imaging or as a MR spectroscopy agent in MR spectroscopy. In another preferred embodiment, the carboxylic acids used in the method of the invention are precursors of an MR imaging agent. For both embodiments, preferred carboxylic acids are endogenous compounds or precursors of endogenous compounds. An example of the latter would be a carboxylic acid like pyruvic acid (a precursor) which is converted to the endogenous compound pyruvate (a derivative, i.e. a salt of a carboxylic acid) by for instance dissolving the solid hyperpolarised pyruvic acid after the DNP process in a base-containing aqueous dissolution medium and using the so-obtained dissolved hyperpolarised pyruvate as MR imaging agent. Preferred are endogenous carboxylic acids or carboxylic acids that are precursors of endogenous compounds, i.e. endogenous derivatives of carboxylic acids that play a role in a metabolic process in the human or non-human animal body. When such hyperpolarised endogenous carboxylic acids or endogenous derivatives of carboxylic acids are used as MR imaging agents one may get information about the metabolic state of a tissue in an in vivo MR investigation, i.e. these agents are useful for in vivo MR imaging and/or MR spectroscopy of metabolic activity. Information of the metabolic status of a tissue might for instance be used to discriminated between healthy (normal) and diseased tissue.

Thus preferred carboxylic acids to be used in the method of the invention are maleic acid, acetic acid, fumaric acid, pyruvic acid, malonic acid, succinic acid, oxaloacetic acid, lactic acid and α-ketoglutaric acid which are precursors for the endogenous compounds malate, acetate, fumarate, pyruvate, malonate, succinate, oxaloacetate, lactate and α-ketoglutarate, which all play a role in a metabolic process in the human or non-human animal body. Another preferred endogenous carboxylic acid that plays a role in a metabolic process in the human or non-human animal body is nicotinic acid. Other preferred endogenous carboxylic acids that play a role in a metabolic process in the human or non-human animal body are amino acids like alanine, glycine, cysteine, proline, tyrosine, sarcosine, GABA or homocysteine. Most preferred carboxylic acids are pyruvic acid, oxaloacetic acid, α-ketoglutaric acid, alanine and glycine.

If endogenous carboxylic acids that play a role in a metabolic process in the human or non-human animal body or carboxylic acids which are precursors of endogenous derivatives of carboxylic acids that play a role in a metabolic process in the human or non-human animal body are used in the method of the invention, these hyperpolarised endogenous carboxylic acids or hyperpolarised endogenous derivatives of carboxylic acids are preferably used as MR imaging agents for in vivo molecular MR imaging and/or chemical shift imaging and/or MR spectroscopy of metabolic activity in the human or non-human animal body. Of these hyperpolarised endogenous carboxylic acids or hyperpolarised endogenous derivatives of carboxylic acids, those are preferred which contain polarised nuclei that exhibit slow longitudinal relaxation so that a fairly high polarisation is maintained for a sufficient length of time for transfer into a human or non-human animal body and subsequent imaging. Preferred endogenous carboxylic acids or endogenous derivatives of carboxylic acids contain nuclei with longitudinal relaxation time constants ($T_1$) that are greater than 10 seconds, preferably greater than 30 seconds and even more preferably greater that 60 seconds at a magnetic field strength of 0.01 to 5 T and a temperature in the range of from 20 to 40° C. Such so called "high $T_1$ agents" are for instance described in WO-A-99/35508. Alternatively, $T_1$ values of possible endogenous carboxylic acids or endogenous derivatives of carboxylic acids may be found in the literature or may be determined by acquiring an NMR spectrum of the possible compound, e.g. a $^{13}C$-NMR spectrum to determine the $T_1$ of a $^{13}C$-labelled possible endogenous carboxylic acids or endogenous derivatives of carboxylic acids.

Generally, the carboxylic acid intended to be used as an MR imaging agent for in vivo MR imaging and/or chemical shift imaging and/or MR spectroscopy or being a precursor for such an agent is preferably an isotopically enriched compound, the isotopic enrichment being more preferably an isotopic enrichment of non-zero spin nuclei (MR active nuclei), suitably $^{15}N$—if present in the compound—and/or $^{13}C$, more preferably $^{13}C$. The isotopic enrichment may include either selective enrichments of one or more sites within the compound or uniform enrichment of all sites with enrichment of one site, preferably at a nucleus with a high $T_1$ value, being preferred. Enrichment can for instance be achieved by chemical synthesis or biological labelling, both methods are known in the art and appropriate methods may be chosen depending on the specific compound to be isotopically enriched.

A preferred embodiment of a carboxylic acid that is intended to be used as a MR imaging agent in vivo or is a precursor for such an agent is a compound that is isotopically enriched in only one position of the molecule, preferably with an enrichment of at least 10%, more suitably at least 25%, more preferably at least 75% and most preferably at least 90%. Ideally, the enrichment is 100%.

The optimal position for isotopic enrichment is dependent on the relaxation time of the MR active nuclei. Preferably, carboxylic acids used in the method of the invention are isotopically enriched in positions with long $T_1$ relaxation time (high $T_1$ values). $^{13}C$-enriched carboxylic acids used in the method of the invention are preferably enriched at a carboxyl-C-atom, a carbonyl-C-atom or a quaternary C-atom. The latter two positions may of course only be enriched if they are present in the carboxylic acid, i.e. if the carboxylic acid contains a carbonyl group (like for instance pyruvic acid or α-ketoglutaric acid) or a quaternary C-atom in addition to the carboxyl group (like for instance citric acid and amino acids, apart from glycine).

Especially preferred carboxylic acids for use as precursors for MR imaging agents are $^{13}C$-pyruvic acid, $^{13}C$-actetic acid, $^{13}C$-oxaloacetic acid and $^{13}C$-α-ketoglutaric acid. These compounds are precursors for $^{13}C$-pyruvate, $^{13}C$-acetate, $^{13}C$-oxaloacetate and $^{13}C$-α-ketoglutarate. Especially preferred carboxylic acids for use as MR imaging agents are further $^{13}C$-alanine and $^{13}C$-glycine, more preferably $^{13}C_1$-alanine and $^{13}C_1$-glycine. $^{13}C$-pyruvic acid is the most preferred carboxylic acid and may be isotopically enriched at the C1-position ($^{13}C_1$-pyruvic acid), at the C2-position ($^{13}C_2$-pyruvic acid), at the C3-position ($^{13}C_3$-pyruvic acid), at the C1-and the C2-position ($^{13}C_{1-2}$-pyruvic acid), at the C1-and the C3-position ($^{13}C_{1-3}$-pyruvic acid), at the C2-and the C3-position ($^{13}C_{2-3}$-pyruvic acid) or at the C1-, C2-and C3-position ($^{13}C_{1,2,3}$-pyruvic acid). The C1-position is the preferred position for the $^{13}C$ isotopic enrichment of pyruvic acid.

In another preferred embodiment, the hyperpolarised carboxylic acids obtained by the method of the invention are used in solid state NMR spectroscopy. Here the hyperpolarised solid carboxylic acid may be analysed by either static or magic angle spinning solid state NMR spectroscopy. In this embodiment, carboxylic acids of any type and molecule size can be used in the method of the invention.

The trityl radical used in the method of the invention works as a DNP agent, which is essential in the DNP method as the large electron spin polarisation of the DNP agent is converted to nuclear spin polarisation of nuclei in the carboxylic acid via microwave irradiation close to the electron Larmor frequency. The microwaves stimulate communication between electron and nuclear spin systems via e-e and e-n transitions. For effective DNP, the DNP agent has to be stable and soluble in the compound to be polarised or in a solution thereof to achieve intimate contact between said compound and the DNP agent. Such an intimate contact is necessary for the aforementioned communication between electron and nuclear spin systems. In this context, stable trityl radicals proved to be highly useful DNP agents. Oxygen-based, sulfur-based or carbon-based stable trityl radicals are for instance described in WO-A-99/35508, WO-A-88/10419, WO-A-90/00904, WO-A-91/12024, WO-A-93/02711 or WO-A-96/39367.

The optimal choice of trityl radical depends on several aspects. As mentioned before, the trityl radical and the compound to be polarised must be in intimate contact during DNP process in order to result in optimal polarisation levels in the compound. Thus, in a preferred embodiment of the invention the trityl radical is soluble in the carboxylic acid or in a solution thereof. The former is suitable option if the carboxylic acid to be polarised is a liquid at room temperature, like for instance pyruvic acid or if the carboxylic acid is transferred into the liquid state, e.g. by melting at elevated temperatures. To prepare a solution of a carboxylic acid, a solvent or a solvent mixture may be used. However if the polarised carboxylic acid is used for in vivo applications like being used as a MR imaging agent for in vivo MR imaging or being a precursor of such an agent, it is preferred to keep the amount of solvent to a minimum or, if possible, to avoid the use of solvents. To be used as an in vivo MR imaging agent, a hyperpolarised compound usually needs to be administered in a relatively high concentration, i.e. a highly concentrated composition comprising the carboxylic acid, a trityl radical, a Gd-chelate of formula (1) is preferably used in the DNP process and hence the amount of solvent is preferably kept to a minimum. In this context, it is also important to keep the mass of the composition preferably as small as possible. A high mass will have a negative impact on the efficiency of the dissolution process, if dissolution is used to liquefy the solid composition comprising the hyperpolarised carboxylic acid after the DNP process, e.g. for use as an MR imaging agent or as a precursor and being converted into a MR imaging agent in that dissolution process. This is due to the fact that for a given volume of dissolution medium in the dissolution process, the ratio of the dissolution medium to mass of the solid composition decreases when the mass of the solid composition increases. Further, using certain solvents may require their removal before the hyperpolarised carboxylic acid or derivative thereof used as an MR imaging agent is administered to the patient since these solvents might not be physiologically tolerable.

If the carboxylic acid used in the method of the invention is a rather lipophilic/hydrophilic compound, the trityl radical should be rather lipophilic/hydrophilic too. Lipophilicity/hydrophilicity of the trityl radical can be influenced by choosing suitable residues which render the trityl radical molecule lipophilic/hydrophilic. Further, the trityl radical has to be stable in presence of the carboxylic acid. Hence if the carboxylic acid used in the method of the invention is a relatively strong acid, like for instance oxalic acid or pyruvic acid, the trityl radical should be stable under strong acidic conditions. If the carboxylic acid further contains reactive groups, a trityl radical should be used which is relatively inert towards these reactive groups. From the aforesaid it is apparent that the choice of trityl radical is highly dependent on the chemical nature of the carboxylic acid used in the method of the invention.

In WO-A-2006/011811, trityl radicals are disclosed which are especially useful DNP agents for the DNP polarisation of acidic organic compounds, i.e. carboxylic acids. Using these trityl radicals in the method of the invention is preferred.

In a preferred embodiment of the method according to the invention, the carboxylic acid is pyruvic acid, more preferred $^{13}C$-pyruvic acid, most preferred $^{13}C_1$-pyruvic acid and the trityl radical is a trityl radical of the formula (2)

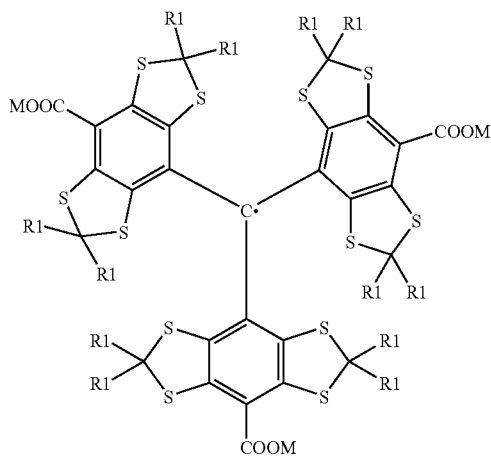

wherein

M represents hydrogen or one equivalent of a cation; and

R1 which is the same or different represents a straight chain or branched $C_1$-$C_6$-alkyl group or a group —$(CH_2)_n$—X—R2, wherein n is 1, 2 or 3;

X is O or S; and

R2 is a straight chain or branched $C_1$-$C_4$-alkyl group.

In a preferred embodiment, M represents hydrogen or one equivalent of a physiologically tolerable cation. The term "physiologically tolerable cation" denotes a cation that is tolerated by the human or non-human animal living body. Preferably, M represents hydrogen or an alkali cation, an ammonium ion or an organic amine ion, for instance meglumine. Most preferably, M represents hydrogen or sodium.

In a further preferred embodiment, R1 is the same, more preferably a straight chain or branched $C_1$-$C_4$-alkyl group, most preferably methyl, ethyl or isopropyl.

In a further preferred embodiment, R1 is the same or different, preferably the same and represents —$CH_2$—$OCH_3$, —$CH_2$—$OC_2H_5$, —$CH_2$—$CH_2$—$OCH_3$, —$CH_2$—$SCH_3$, —$CH_2$—$SC_2H_5$ or —$CH_2$—$CH_2$—$SCH_3$, most preferably —$CH_2$—$CH_2$—$OCH_3$.

In a more preferred embodiment, M represents hydrogen or sodium and R1 is the same and represents —$CH_2$—$CH_2$—$OCH_3$.

The trityl radicals used in the method of the invention may be synthesized as described in detail in WO-A-88/10419, WO-A-90/00904, WO-A-91/12024, WO-A-93/02711, WO-A-96/39367 and WO-A-2006/011811.

As stated above, the Gd-chelates used in the method of the invention are the Gd-chelates of formula (1):

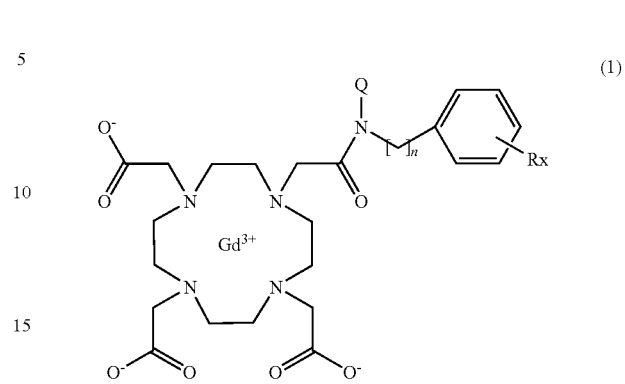

wherein n is 1 to 10;

x is 0 to 10;

R is identical or different and represents fluoro, a straight chain or branched $C_1$-$C_6$-alkyl group, or an aromatic or non-aromatic cyclic group containing 5 to 10 carbon atoms; and Q is H, a straight chain or branched $C_1$-$C_6$-alkyl group, or an aromatic or non-aromatic cyclic group containing 5 to 10 carbon atoms or

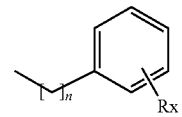

wherein n, x and R are as defined above.

In a preferred embodiment, Q is H, a straight chain or branched $C_1$-$C_6$-alkyl group, preferably methyl, ethyl, propyl, isopropyl, butyl, iso-butyl or tert-butyl or Q is identical with

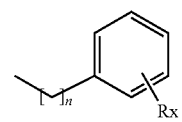

In a preferred embodiment of the embodiment above, n is 1 to 5 and more preferably 1 to 3.

If R is a straight chain or branched $C_1$-$C_6$-alkyl group, R is preferably methyl, ethyl, propyl, isopropyl, butyl, iso-butyl or tert-butyl.

If R is an aromatic or non-aromatic cyclic group containing 5 to 10 carbon atoms, R is preferably cyclopentyl, cyclohexyl, methylcyclopentyl, methylcyclohexyl, benzyl, phenyl or tolyl.

In one embodiment, x is 3 and the three R groups which are identical or different are preferably attached in the ortho-positions and in the para-position. Examples of such an embodiment are the following moieties:

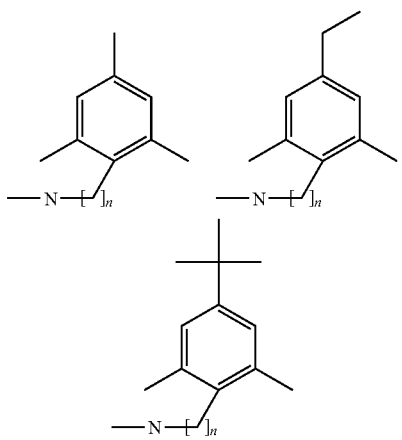

wherein the moieties above correspond to the framed moiety of the Gd-chelate of formula (1) as displayed below:

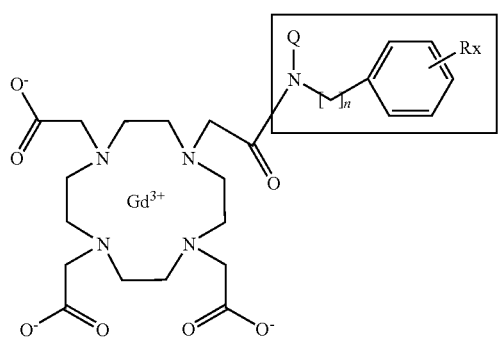

In another embodiment, x is 2 and the two R groups which are identical or different, preferably identical, are preferably attached in the meta-positions. Preferred examples of such an embodiment are the following moieties, wherein the moieties correspond to the framed moiety of the Gd-chelate of formula (1) as displayed above:

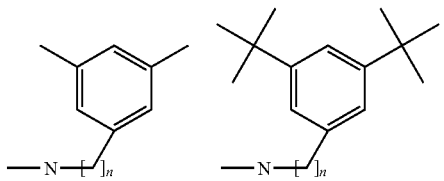

In a preferred embodiment, x is 1 and the R group is preferably attached in the para-position. In this embodiment, R is preferably selected from fluoro, methyl, isopropyl, isobutyl and tert-butyl, most preferably selected from methyl and tert-butyl.

In another preferred embodiment, x is 0 and n is 1 to 5, preferably 1 to 3.

The Gd-chelates of formula (1) are suitably synthesized by using as a chelator a DO3A derivative with protected carboxylic groups as the starting material. Suitable DO3A derivatives are for instance 1,4,7-Tris(tert-butoxycarbonylmethyl)-1,4,7,10-tetraaza-cyclododecane or 1,4,7-Tris(benzyloxycarbonylmethyl)-1,4,7,10-tetraaza-cyclodo-decane.

These DO3A derivatives may be prepared by known methods such as described in U.S. Pat. No. 4,885,363 or WO-A-96/28433, which are incorporated herein by reference.

The DO3A derivatives may be reacted in a solvent and in the presence of a base with a compound of formula (3)

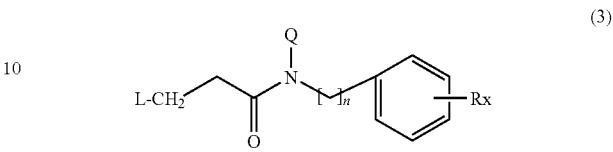

wherein L is a leaving group such as halogen, preferably chloride and Q, n, x and R are as defined above.

Compounds of formula (3) may be obtained by reaction of Rx-substituted amines or—in case of x being 0—amines with 2-halogenacetyl chloride, preferably 2-chloroacetyl chloride, in a solvent and in the presence of a base. Methods to synthesise Rx-substituted amines and amines are known in the art and a variety of such Rx-substituted amines and amines are commercially available.

After having removed present protection groups, e.g. for instance by reaction with trifluoroacetic acid in case of a DO3A derivative with tert-butoxy protected carboxylic groups, the chelator of formula (1a)

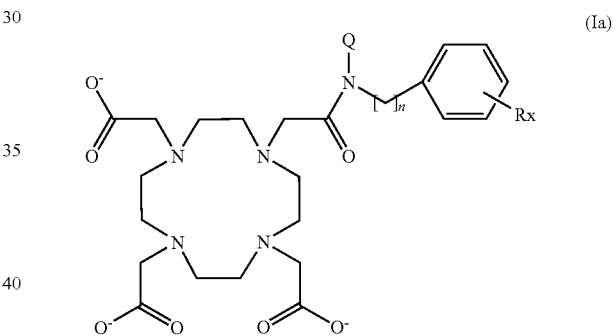

wherein Q, n, x and R are as defined above is reacted with a suitable $Gd^{3+}$-compound like $Gd_2O_3$ or $Gd^{3+}$salts like $GdCl_3$ in a suitable solvent, e.g. water to result in the Gd-chelates of formula (1). Other suitable ways of synthesising the chelators of formula (1a) and the compounds of formula (3) are described in U.S. Pat. No. 5,737,752 the content of which is enclosed by reference herein.

The Gd-chelates of formula (1) are especially useful in the DNP polarisation of carboxylic acids since these Gd-chelates are stable in the presence of such acids. This is an important feature since complex dissociation of the Gd-chelate (dechelation) will lead to free $Gd^{3+}$ ions with detrimental consequences on the polarisation. Polarisation decays much more rapidly in the presence of free paramagnetic metal ions like $Gd^{3+}$ ions which dramatically shorten the "life time" of a hyperpolarised compound that is intended to be used as an MR imaging agent.

If the carboxylic acid to be polarised is a liquid or dissolved in a solvent, it is preferred to use a Gd-chelate of the formula (1) which is soluble in the liquid carboxylic acid or the solution thereof. If the carboxylic acid to be polarised is rather lipophilic, the Gd-chelate of formula (1) should be rather lipophilic too. Lipophilicity may be influenced by choosing the appropriate type and number of R groups.

Optionally, the composition used in the method of the invention which comprises the carboxylic acid, a trityl radical and a Gd-chelate of formula (1) further comprises a chelator and/or a Ca-chelate.

The term "chelator" denotes a chemical entity that binds (complexes) a metal ion, e.g. $Gd^{3+}$, to form a chelate.

A chelator may be added to the composition to avoid any free $Gd^{3+}$ ions in the liquid composition after having dissolved or melted the solid composition comprising the hyperpolarised carboxylic acid or a derivative thereof after the DNP process. As stated earlier, free $Gd^{3+}$ ions have detrimental consequences on the polarisation since polarisation decays much more rapidly in the presence of free paramagnetic metal ions like $Gd^{3+}$ ions. This in turn dramatically shortens the "life time" of a hyperpolarised carboxylic acid or a derivative thereof as an MR imaging agent. Additional chelator present in the composition reacts with free $Gd^{3+}$ ions to from a Gd-chelate and hence free $Gd^{3+}$ ions are "scavenged" from the composition once it is liquefied (i.e. dissolved or melted). Suitable chelators are those which readily and quickly form complexes with $Gd^{3+}$ ions, preferably EDTA, DOTA-BOM or DTPA-BMA. These chelators and their synthesis are known in the art. In another preferred embodiment, a chelator of formula (1a) is used.

Instead of a chelator, a Ca-chelate comprising a chelator as described above may be added to the composition. The effect is similar to the addition of a chelator since Ca-chelates are weak complexes. In the presence of free $Gd^{3+}$ ions, an exchange between $Ca^{2+}$ ions and $Gd^{3+}$ ions occurs since chelators as described above form much stronger complexes with $Gd^{3+}$ than with $Ca^{2+}$. Free $Ca^{2+}$ ions however do not have the detrimental consequences on the polarisation as described above since they are not paramagnetic ions. Preferred Ca-chelates are thus Ca-EDTA, Ca-DOTA-BOM and Ca-DTPA-BMA. In another preferred embodiment, a Ca-chelate of formula (1b) is used:

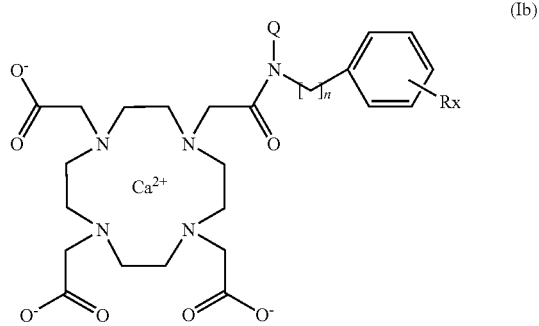

(Ib)

wherein Q, n, x and R are as defined above.

Alternatively, the composition used in the method of the invention may contain both, a chelator and a Ca-chelate. The chelator may be identical or different than the chelator of the Ca-chelate, e.g. the chelator may be EDTA and the Ca-chelate may Ca-EDTA. In another embodiment, the chelator may be EDTA and the Ca-chelate may be Ca-DTPA-BMA. In a preferred embodiment, the chelator is the chelator of formula (1a) and the Ca-chelate is the Ca-chelate of formula (1b).

For carrying out the method according to the invention, a composition comprising a carboxylic acid, a trityl radical, a Gd-chelate of formula (1) and optionally a chelator and/or a Ca-chelate is prepared.

If the carboxylic acid used in the method of the invention is a liquid at room temperature, like for instance pyruvic acid, said liquid carboxylic acid is combined with the chosen trityl radical and the chosen Gd-chelate of formula (1) and optionally with a chelator and/or a Ca-chelate to form a composition where the all components of that composition are in intimate contact. Preferably, the chosen trityl radical, the Gd-chelate of formula (1) and the optional chelator and/or Ca-chelate are soluble in the liquid carboxylic acid. Alternatively but less preferred, a solution of the chosen trityl radical and/or a solution of the chosen Gd-chelate of formula (1) and/or a solution of the optional chelator and/or Ca-chelate can be prepared in a suitable solvent(s), e.g. water, which is then added to the liquid carboxylic acid. Intimate mixing can be further promoted by several means known in the art, such as stirring, vortexing or sonication.

If the carboxylic acid used in the method of the invention is a solid at room temperature, it may be melted—provided that no degradation of the carboxylic acid occurs—and the melted carboxylic acid is combined with the chosen trityl radical, the chosen Gd-chelate of formula (1) and optionally with a chelator and/or a Ca-chelate as described in the previous paragraph.

In another embodiment, a solution of the solid carboxylic acid may be prepared, e.g. by dissolving the carboxylic acid in a suitable solvent or solvent mixture, preferably in a solvent which is a good glass former to prevent crystallization of the composition upon cooling/freezing. Suitable glass formers are for instance glycerol, propanediol or glycol. Subsequently, the dissolved carboxylic acid is combined with the chosen trityl radical, Gd-chelate of formula (1) and optionally with a chelator and/or a Ca-chelate, preferably all as dry components. Alternatively but less preferred, a solution of the chosen trityl radical and/or a solution of the chosen Gd-chelate of formula (1) and/or a solution of the optional chelator and/or Ca-chelate can be prepared in a suitable solvent(s), e.g. water, which is then added to the dissolved carboxylic acid. Glass formers may also be added to carboxylic acids dissolved in non-glass forming solvents to prevent the composition from crystallizing upon cooling/freezing. However, as stated earlier, the addition of solvents and/or glass formers should be kept to the necessary minimum. Hence the preferred way is to select a trityl radical, a Gd-chelate of formula (1) and optionally a chelator and/or a Ca-chelate which are soluble in or miscible with the carboxylic acid, provided that the carboxylic acid is a liquid at room temperature or can be melted without degradation.

Suitably, the concentration of trityl radical is 5 to 25 mM, preferably 10 to 20 mM in the composition. Regarding the concentration of Gd-chelate of formula (1), 0.1 to 8 mM in the composition is suitable and concentrations of 0.1 to 6 mM and 0.5 to 4 mM are preferred and more preferred, respectively. If a chelator and/or a Ca-chelate are present in the composition to be used in the method of the invention, the concentration of said chelator and/or Ca-chelate in said composition is suitably 0.1 to 10 mM, preferably 0.5 to 8 mM and more preferably 1.5 to 7 mM.

The composition is cooled and/or frozen, preferably in such a way that crystallization is prohibited. Cooling/freezing may be achieved by methods known in the art, e.g. by freezing the composition in a freezer or in liquid nitrogen or by simply placing it in the DNP polariser, where liquid helium will freeze it.

In one embodiment, the composition is degassed before cooling/freezing. Degassing may be achieved by bubbling helium gas through the composition (e.g. for a time period of 2-15 min) but can be effected by other known common methods.

According to the method of the invention, the composition undergoes dynamic nuclear polarisation, DNP. The DNP technique is for instance described in WO-A-98/58272 and in WO-A-01/96895, both of which are included by reference herein. Generally, a moderate or high magnetic field and a very low temperature are used in the DNP process, e.g. by carrying out the DNP process in liquid helium and a magnetic field of about 1 T or above. Alternatively, a moderate magnetic field and any temperature at which sufficient polarisation enhancement is achieved may be employed. In a preferred embodiment, the DNP process is carried out in liquid helium and a magnetic field of about 1 T or above. Suitable polarisation units (=polarisers) are for instance described in WO-A-02/37132. In a preferred embodiment, the polarisation unit comprises a cryostat and polarising means, e.g. a microwave chamber connected by a wave guide to a microwave source in a central bore surrounded by magnetic field producing means such as a superconducting magnet. The bore extends vertically down to at least the level of a region "P" near the superconducting magnet where the magnetic field strength is sufficiently high, e.g. between 1 and 25 T, for polarisation of the sample nuclei to take place. The bore for the probe, i.e. the composition to be polarised, is preferably sealable and can be evacuated to low pressures, e.g. pressures in the order of 1 mbar or less. A probe introducing means such as a removable transporting tube can be contained inside the bore and this tube can be inserted from the top of the bore down to a position inside the microwave chamber in region P. Region P is cooled by liquid helium to a temperature low enough to for polarisation to take place, preferably temperatures of the order of 0.1 to 100 K, more preferably 0.5 to 10 K, most preferably 1 to 5 K. The probe introducing means is preferably sealable at its upper end in any suitable way to retain the partial vacuum in the bore. A probe-retaining container, such as a probe-retaining cup, can be removably fitted inside the lower end of the probe introducing means. The probe-retaining container is preferably made of a light-weight material with a low specific heat capacity and good cryogenic properties such, e.g. KelF (polychlorotrifluoroethylene) or PEEK (polyetheretherketone) and it may be designed in such a way that it can hold more than one probe.

The probe is inserted into the probe-retaining container, submerged in the liquid helium and irradiated with microwaves, preferably at a frequency of about 94 GHz at 200 mW. The level of polarisation may be monitored as disclosed on page 6 of this application.

In a preferred embodiment, the solid hyperpolarised carboxylic acid produced by the method of the invention is liquefied in a subsequent step.

Thus in a preferred embodiment, the method of the invention is a method for producing a liquid composition comprising a hyperpolarised carboxylic acid or a derivative thereof, said method comprising preparing a composition comprising the carboxylic acid, a trityl radical and a Gd-chelate of formula (1); carrying out dynamic nuclear polarisation on the composition; and liquefying the composition.

Optionally, the composition above comprises a chelator and/or a Ca-chelate.

In the context of the invention, the term "hyperpolarised carboxylic acid" denotes the carboxylic acid which has been used to prepare the aforementioned composition and which is—after having carried out the method as described above—hyperpolarised. The term "derivative of a hyperpolarised carboxylic acid" denotes a hyperpolarised chemical entity which is derived from the hyperpolarised carboxylic acid by liquefying the composition by dissolving the hyperpolarised carboxylic acid in a dissolution medium which converts it to a different hyperpolarised chemical entity. An example would be the dissolution of the hyperpolarised carboxylic acid in a base and thus converting the carboxyl group into a carboxylate group, for instance converting hyperpolarised pyruvic acid into hyperpolarised pyruvate or hyperpolarised acetic acid into hyperpolarised acetate.

Liquefaction is carried out either by dissolving the solid composition after the DNP process in an appropriate solvent or solvent mixture, e.g. an aqueous carrier like a buffer solution or by melting it, optionally with a subsequent dissolution step or a dilution step in a suitable solvent or solvent mixture. Suitable methods and devices for the dissolution of a hyperpolarised solid composition are for instance described in WO-A-02/37132. Suitable methods and devices for the melting of a hyperpolarised solid composition are for instance described in WO-A-02/36005. If the hyperpolarised carboxylic acid or a derivative thereof is intended to be used as a MR imaging agent, the solid composition containing the hyperpolarised carboxylic acid is dissolved, preferably in an aqueous carrier or suitable solvent, to result in a physiologically tolerable solution.

As explained earlier, the dissolution medium used for the dissolution of the solid composition containing the hyperpolarised carboxylic acid may also be of such a nature as to convert the hyperpolarised carboxylic acid to a different hyperpolarised chemical entity (derivative). In this case, the hyperpolarised carboxylic acid is denoted a precursor. If for instance a dissolution medium containing a base is used to dissolve a solid composition comprising the hyperpolarised carboxylic acid, said hyperpolarised carboxylic acid is neutralized and converted to a hyperpolarized carboxylate. Thus, the hyperpolarised compound in the liquid composition would be a salt of the carboxylic acid and no longer the carboxylic acid itself.

In an optional subsequent step, the trityl radical and/or the Gd-chelate of formula (1) and/or optionally present chelator and/or Ca-chelate and/or Gd-chelate, i.e. Gd-chelate which is a reaction product of the chelator or Ca-chelate with free $Gd^{3+}$ ions are removed from the liquefied composition. If the hyperpolarised carboxylic acid or derivative thereof is intended to be used as a MR imaging agent in a living human or animal being, the trityl radical, the Gd-chelate of formula (1) and optionally present chelator and/or Ca-chelate and/or Gd-chelate thereof (hereinafter also denoted "aforementioned compounds") are preferably removed from the liquefied composition.

Methods useful to remove the trityl radical, Gd-chelate of formula (1), chelator and/or Ca-chelate and/or Gd-chelate are known in the art. Generally, the applicable methods depend on the exact nature and chemical properties of the aforementioned compounds which have been used to prepare the composition used in the method of the invention. Upon dissolution or melting of the solid composition containing the hyperpolarised carboxylic acid, the trityl radical and/or the Gd-chelate of formula (1) and/or the chelator and/or Ca-chelate and/or Gd-chelate might precipitate and thus may easily be separated from the liquid composition by filtration. Whether precipitation occurs or not is of course dependent on the nature of the solvent and the aforementioned compounds.

If no precipitation occurs, the trityl radical, the Gd-chelate of formula (1), chelator, Ca-chelate and Gd-chelate may be removed by chromatographic separation techniques, e.g. liquid phase chromatography like reversed phase chromatography, (solid phase) extraction or other chromatographic separation methods known in the art. In general, it is preferred to use a method which is able to remove all the aforementioned compounds in one step as polarisation in the hyperpolarised carboxylic acid or derivative thereof in the liquid composition decays due to $T_1$ relaxation. The faster the aforementioned compounds are removed from the liquid composition the higher the polarisation level retained. Hence not only from the point of having an intimate contact between the carboxylic acid to be polarised, the trityl radical and the Gd-chelate of formula (1) but also from the point of a fast and efficient removal it is beneficial to select a trityl radical and a Gd-chelate of formula (1) which have similar chemical properties. This of course also applies for the choice of chelate and/or Ca-chelate, should those compounds be used in the composition for use in the method of the invention. If for instance a rather lipophilic trityl radical and a rather lipophilic Gd-chelate of formula (1) are used, and optionally a rather lipophilic chelator and/or Ca-chelate are used, all could be removed in one step by reversed phase liquid chromatography on a single chromatography column.

After removal of the aforementioned compounds, the liquid composition may be checked for residual trityl radical and/or Gd-chelate of formula (1) and for residual amounts of the optionally present chelator, Ca-chelate and Gd-chelate.

As trityl radicals have a characteristic UV/visible absorption spectrum, it is possible to use UV/visible absorption measurement as a method to check for their presence in the liquid composition after their removal. In order to obtain quantitative results, i.e. the concentration of the trityl radical present in the liquid composition, the optical spectrometer can be calibrated such that absorption at a specific wavelength from an aliquot of the liquid composition yields the corresponding trityl radical concentration in the liquid composition.

Due to the presence of the aromatic group in the Gd-chelates of formula (1) UV/visible absorption measurement can also be used as a method to check for the presence of Gd-chelate of formula (1). Again quantitative results may be obtained by calibrating the spectrometer as described in the previous paragraph. If a chelator of formula (1b) and/or a Ca-chelate of formula (1b) have been used in the composition to be used in the method of the invention, the same UV/visible absorption measurement can also be used as a method to check for the presence of these compound since all of them comprise an aromatic group.

In a preferred embodiment, the method of the invention is used for the production of a liquid MR imaging agent and the composition used in the method of the invention is liquefied by dissolution, preferably by dissolution in a physiologically tolerable aqueous carrier like a buffer solution.

In a further preferred embodiment of the method according to the invention the composition comprises $^{13}$C-pyruvic acid, preferably $^{13}C_1$-pyruvic acid, a trityl radical of formula (2) and a Gd-chelate of formula (1). Since $^{13}C_1$-pyruvic acid is a rather lipophilic compound, a rather lipophilic trityl radical of formula (2) and a rather lipophilic Gd-chelate of formula (1) are preferably chosen.

In a more preferred embodiment, a trityl radical of formula (2) is used wherein M represents hydrogen or sodium and R1 is the same and represents —$CH_2$—$CH_2$—$OCH_3$ and a Gd-chelate of formula (1) is used wherein Q is H, n is 1 to 3, x is 0 or 1 and the R group, if present, is attached in the para-position. In a very preferred embodiment, Q is H, n is 1 to 3, x is 1 and R, which is attached in the para-position is methyl, isopropyl, isobutyl and tert-butyl, most preferred methyl and tert-butyl. These Gd-chelates of formula (1) are not only especially useful in the DNP polarisation of pyruvic acid since they are stable in the presence of pyruvic acid, but they can be removed together with the trityl radical of formula (2) in a single step. Optionally a chelator of formula (1a) and/or a Ca-chelate of formula (1b) are added to the composition.

In this preferred embodiment, the composition is prepared by dissolving the aforementioned trityl radical, Gd-chelate of formula (1) and the optional chelator (1a) and/or Ca-chelate (1b) in $^{13}$C-pyruvic acid. The components of the composition are thoroughly mixed and the composition is cooled and/or frozen. After dynamic nuclear polarisation, the solid composition comprising the hyperpolarised $^{13}$C-pyruvic acid is dissolved or melted and then converted to hyperpolarised $^{13}$C-pyruvate or dissolved and converted simultaneously.

In one embodiment, the solid composition containing hyperpolarised $^{13}$C-pyruvic acid is reacted with a liquid base to simultaneously dissolve and convert it to $^{13}$C-pyruvate and subsequently a buffer solution, preferably a physiologically tolerable buffer solution, is added to finalise dissolution and optionally convert residual $^{13}$C-pyruvic acid to $^{13}$C-pyruvate. In a preferred embodiment, the base is an aqueous solution of NaOH, $Na_2CO_3$ or $NaHCO_3$, more preferably of NaOH. Suitably, the buffer solution is a physiologically tolerable buffer solution containing buffers that buffer in the range of about pH 7 to 8 like for instance phosphate buffer ($KH_2PO_4$/ $Na_2HPO^4$), ACES, PIPES, imidazole/HCl, BES, MOPS, HEPES, TES, TRIS, HEPPS or TRICIN. Preferably, a TRIS buffer solution, a citrate buffer solution or a phosphate buffer solution is used. The buffer solution may further comprise chelators like EDTA, DTPA-BMA or DOTA-BOM to complex any free $Gd^{3+}$ ions which may be present. In another preferred embodiment the buffer solution and the base are combined into one alkaline solution and this solution is added to the solid composition containing the hyperpolarised $^{13}$C-pyruvic acid, dissolving and converting the $^{13}$C-pyruvic acid into $^{13}$C-pyruvate at the same time.

The Gd-chelate of formula (1), the trityl radical of formula (2) and the optional chelator of formula (1a) and/or Ca-chelate of formula (1b) mentioned above are preferably removed, suitably by using reversed phase liquid chromatography, since this allows for the simultaneous removal of all the aforementioned compounds.

Optionally, the liquid composition comprising hyperpolarised $^{13}$C-pyruvate is checked for residual aforementioned compounds, e.g. using the methods described earlier in this application.

To be used as an agent for in vivo MR imaging, the liquid composition comprising a hyperpolarised carboxylic acid or a derivative thereof obtained by the method of the invention is provided as a composition, i.e. an imaging medium, that is suitable for the administration to a living human or non-human animal body. The imaging medium preferably comprises physiologically tolerable aqueous carriers like a buffer solution, water or saline as described above. The imaging medium may further comprise conventional pharmaceutically acceptable carriers, excipients and formulation aids. Thus, the imaging medium may for example include stabilizers, osmolality adjusting agents, solubilising agents and the like.

An imaging medium comprising the liquid composition comprising a hyperpolarised carboxylic acid or a derivative thereof obtained by the method of the invention which is used for in vivo MR imaging, i.e. in a living human or non-human animal body, is preferably administered to said body parenterally, preferably intravenously.

Generally, the living human or non-human animal body under examination is positioned in an MR magnet. Dedicated MR-RF-coils are positioned to cover the area of interest. Dosage and concentration of the imaging medium will depend upon a range of factors such as toxicity and the administration route. At less than 400 s after the administration, preferably less than 120 s, more preferably less than 60 s after the administration, especially preferably 20 to 50 s an MR imaging sequence is applied that encodes the volume of interest.

To be used as an agent for in vitro NMR assays or for MR imaging or MR spectroscopy of ex vivo tissue or isolated organs, the liquid composition comprising a hyperpolarised carboxylic acid or a derivative thereof obtained by the method of the invention is provided as a composition, i.e. an imaging medium that is suitable for being added to for instance isolated proteins like receptors, enzymes, cell cultures, samples derived from a human or non human body (e.g. blood, urine or saliva), ex vivo tissues like biopsy tissues or isolated organs. As it is apparent for the skilled person, pharmaceutically acceptable carriers, excipients and formulation aids may be present in the imaging medium but are not required to be present for such a purpose, and the imaging medium thus preferably comprises an aqueous carrier like a buffer solution or a mixture of buffers solutions as described above and—especially for in vitro NMR—one or more non aqueous solvents like DMSO or methanol.

An imaging medium comprising a liquid composition comprising a hyperpolarised carboxylic acid or a derivative thereof may be used as a "conventional" MR imaging medium, i.e. providing contrast enhancement for anatomical imaging. If the hyperpolarised carboxylic acid or derivative thereof is a compound which plays a role in a metabolic pathway in the human or non-human animal body, said imaging medium may be used for in vivo metabolic MR imaging, thus providing information about the metabolic state of the tissue under examination.

As stated earlier, pyruvate is a compound in the citric acid cycle and thus hyperpolarised $^{13}$C-pyruvate may be used as an imaging agent for tumour imaging as disclosed in detail in WO-A-2006/011810.

Further, the use of hyperpolarised $^{13}$C-pyruvate as an imaging agent for assessing the viability of myocardial tissue has been described in detail in WO-A-2006/054903.

Another aspect of the invention is a composition comprising a carboxylic acid, a trityl radical, a Gd-chelate of formula (1) and optionally a chelator and/or a Ca-chelate. Preferably, said composition is for use in dynamic nuclear polarisation. Preferred embodiments of said composition, i.e. preferred carboxylic acids, trityl radicals and Gd-chelates of formula (1) have been disclosed earlier in this application.

Yet another aspect of the invention is a composition comprising a hyperpolarised carboxylic acid or derivative thereof, preferably a salt of a carboxylic acid, a trityl radical, a Gd-chelate of formula (1) and optionally a chelator and/or a Ca-chelate wherein the composition is obtained by dynamic nuclear polarisation. In a further preferred embodiment, said composition is a liquid composition which is obtained by dynamic nuclear polarisation and subsequent dissolution or melting of the solid composition obtained by said dynamic nuclear polarisation.

Yet another aspect of the invention is a polarising agent comprising a trityl radical and Gd-chelate of formula (1). Preferably, said polarising agent is used for polarising carboxylic acids by dynamic nuclear polarisation.

Yet another aspect of the invention are novel Gd-chelates of formula (1):

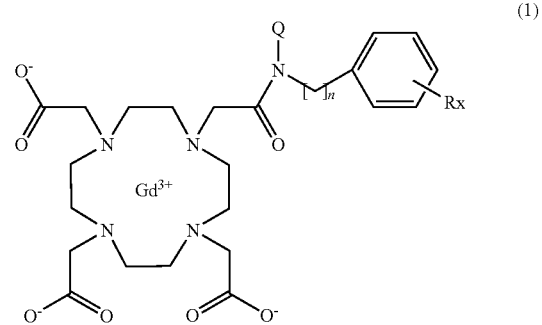

wherein
n is 1 to 10;
x is 0 to 3;
R is identical or different and represents fluoro, a straight chain or branched $C_1$-$C_6$-alkyl group, or an aromatic or non-aromatic cyclic group containing 5 to 10 carbon atoms; and
Q is H, a straight chain or branched $C_1$-$C_6$-alkyl group, or an aromatic or non-aromatic cyclic group containing 5 to 10 carbon atoms or

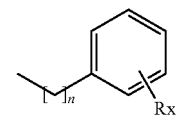

wherein n, x and R are as defined above.

Preferred embodiments of the Gd-chelate of formula (1) are described earlier in the application.

The novel Gd-chelates according to the invention may be used in the dynamic nuclear polarisation of carboxylic acids, as described in this application. They may however also be used as MR active compounds, i.e. imaging agents in a contrast medium used in MR imaging.

Yet another aspect of the invention are novel chelators of formula (1a)

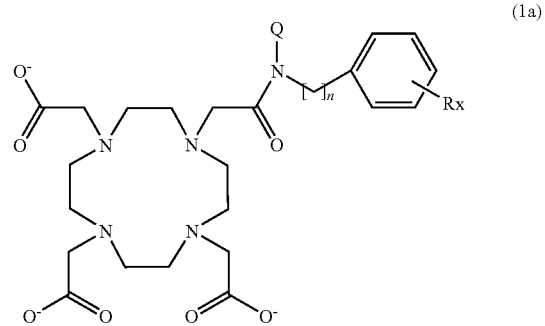

wherein
n is 1 to 10;
x is 0 to 3;
R is identical or different and represents fluoro, a straight chain or branched $C_1$-$C_6$-alkyl group, or an aromatic or non-aromatic cyclic group containing 5 to 10 carbon atoms, with the proviso that if Q is H and x is 0, n is 2 to 10, preferably 2 to 5 and more preferably 2 to 3; and Q is H, a straight chain or branched $C_1$-$C_6$-alkyl group, or an aromatic or non-aromatic cyclic group containing 5 to 10 carbon atoms or

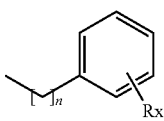

wherein n, x and R are as defined above.

Preferred embodiments of the chelator of formula (1a) are identical with the preferred embodiments of the Gd-chelates of formula (1) and are described earlier in the application.

Yet another aspect of the invention is a method to prepare the above-mentioned chelators of formula (1a) by reacting a DO3A derivative with protected carboxylic groups, preferably 1,4,7-tris(tert-butoxycarbonylmethyl)-1,4,7,10-tetraazacyclodo-decane in a solvent and in the presence of a base with a compound of formula (3)

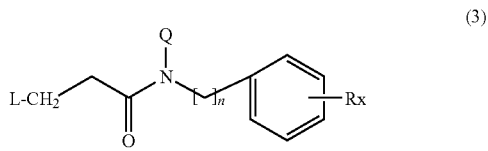

(3)

wherein L is a leaving group such as halogen, preferably chloride and Q, n, x and R are as defined for formula (1a) before and subsequent removal of the protection groups.

Yet another aspect of the invention is a method to prepare Gd-chelates of formula (1) by reacting a) a DO3A derivative with protected carboxylic groups, preferably 1,4,7-tris(tert-butoxycarbonylmethyl)-1,4,7,10 tetraazacyclododecane, in a solvent and in the presence of a base with a compound of formula (3)

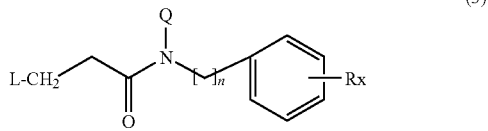

(3)

wherein L is a leaving group such as halogen, preferably chloride and Q, n, x and R are as defined for formula (1) before b) removal of the protection groups; and c) reacting the reaction product of step b) with a $Gd^{3+}$-compound, preferably $GdCl_3$ in a solvent, preferably water.

Yet another aspect of the invention is a kit comprising instructions for use and one or more vials containing a composition comprising a carboxylic acid, a trityl radical and a Gd-chelate of formula (1) and further optionally a chelator and/or a Ca-chelate for use in dynamic nuclear polarisation. In one embodiment, said kit comprises a single vial containing a composition comprising the carboxylic acid, the trityl radical and the Gd-chelate of formula (1) and optionally a chelator and/or a Ca-chelate. In another embodiment, said kit comprises a first vial containing a composition comprising the carboxylic acid and the trityl radical and a second vial containing the Gd-chelate of formula (1) and optionally a chelator and/or a Ca-chelate. The content of said first vial and said second vial are combined before said dynamic nuclear polarisation. The composition in said vial(s) may be a composition of dry matter, i.e. all compounds may be solids. Alternatively, the composition may be a liquid composition, i.e. the compounds may be dissolved in a solvent or, if one of the compounds is a liquid, said compounds may be dissolved in said liquid compound.

In a preferred embodiment, the kit according to the invention comprises instructions for use and a vial containing a composition containing $^{13}C$-pyruvic acid, preferably $^{13}C_1$-pyruvic acid, a trityl radical of formula (2), a Gd-chelate of formula (1) and optionally a chelator and/or a Ca-chelate for use in dynamic nuclear polarisation.

EXAMPLES

Example 1a

Synthesis of the trityl radical Tris (8-carboxy-2,2,6,6-(tetra(methoxyethyl)benzo-[1,2-4,5']bis-(1,3)dithiole-4-yl)methyl sodium salt, a trityl radical of formula (2)

10 g (70 mmol) Tris (8-carboxy-2,2,6,6-(tetra (hydroxyethyl)benzo-[1,2-4,5']-bis-(1,3)-dithiole-4-yl)methyl sodium salt which had been synthesized according to Example 7 of WO-A1-98/39277 were suspended in 280 ml dimethylacetamide under an argon atmosphere. Sodium hydride (2.75 g) followed by methyl iodide (5.2 ml) was added and the reaction which is slightly exothermic was allowed to proceed for 1 hour in a 34° C. water bath for 60 min. The addition of sodium hydride and methyl iodide was repeated twice with the same amounts of each of the compounds and after the final addition, the mixture was stirred at room temperature for 68 hours and then poured into 500 ml water. The pH was adjusted to pH>13 using 40 ml of 1 M NaOH (aq) and the mixture was stirred at ambient temperature for 15 hours to hydrolyse the formed methyl esters. The mixture was then acidified using 50 ml 2 M HCl (aq) to a pH of about 2 and 3 times extracted the ethyl acetate (500 ml and 2×200 ml). The combined organic phase was dried over $Na_2SO_4$ and then evaporated to dryness. The crude product (24 g) was purified by preparative HPLC using acetonitrile/water as eluents. The collected fractions were evaporated to remove acetonitrile. The remaining water phase was extracted with ethyl acetate and the organic phase was dried over $Na_2SO_4$ and then evaporated to dryness. Water (200 ml) was added to the residue and the pH was carefully adjusted with 0.1 M NaOH (aq) to 7, the residue slowly dissolving during this process. After neutralization, the aqueous solution was freeze dried.

Example 2

Synthesis of 1,4,7-Tris(carbonylmethyl)-10-(4-tert-butyl)-benzylaminocarbonylmethyl)-1,4,7,10-tetraazacyclododecane, a chelator of formula (1a)

All chemicals were purchased from Sigma-Aldrich or Fluka. 1,4,7-Tris(tert-butoxycarbonylmethyl)-1,4,7,10-tetraazacyclododecane was prepared as described in WO-A-96/28433.

2a Preparation of 2-Chloro-N-(4-tert-butylphenylmethyl)-acetamide

To a suspension of commercially available 4-tert-butylbenzylamine (8.16 g, 50 mmol) and potassium carbonate (7.95 g, 57.5 mmol) in dichloromethane (100 ml) was added drop wise a solution of 2-chloroacetyl chloride (6.21 g, 55 mmol) in dichloromethane (25 ml) at room temperature. After stirring the reaction mixture at room temperature for 30 min, the reaction mixture was refluxed for 4 h. The reaction mixture was cooled and water (100 ml) was added. The phases were separated and the organic phase was dried over $MgSO_4$ and evaporated in vacuo. The title compound was obtained as a white crystalline material which was used in the next step without any further purification.

2b Preparation of 1,4,7-Tris(tert-butoxycarbonylmethyl)-10-((4-tert-butyl)-benzylaminocarbonylmethyl)-1,4,7,10-tetraazacyclodo-decane A reaction mixture of 1,4,7-tris(tert-butoxycarbonylmethyl)-1,4,7,10-tetraaza-cyclododecane (7.57 g, 12.7 mmol), 2-chloro-N-(4-tert-butylphenylmethyl)-acetamide (3.60 g, 15 mmol) obtained from Example 2a and potassium carbonate (5.53 g, 40 mmol) in acetonitrile (100 ml) was heated to 75° C. and stirred under nitrogen-atmosphere overnight. The reaction mixture was cooled to room temperature and filtered. The filtrate was evaporated in vacuo and the residue was submitted to flash-chromatography (silica, $MeOH/CHCl_3$). The fractions containing the product were combined and evaporated in vacuo resulting in the title compound being a yellow oil that crystallised upon storage.

2c 1,4,7-Tris(carbonylmethyl)-10-((4-tert-butyl)benzylamino-carbonylmethyl)-1,4,7,10-tetraazacyclododecane 1,4,7-Tris(tert-butoxycarbonylmethyl)-10-(4-tert-butyl)benzylaminocarbonyl-methyl)-1,4,7,10-tetraazacyclododecane (3.59 g, 5 mmol) from Example 2b was dissolved in trifluoroacetic acid (25 ml) under nitrogen-atmosphere. The reaction was stirred at room temperature overnight and then evaporated in vacuo. The residue was dissolved in water (10 ml) and evaporated in vacuo. The residue was re-dissolved in water (10 ml), a cross linked poly-4-vinylpyridine (Reillex™ 425, 5.2 g) was added and the mixture was stirred for 20 min before being filtrated. The filtrate was submitted to freeze-drying giving the title compound as a white hygroscopic material.

In a similar way, other chelators of formula (1a) were prepared starting from the following amines and Rx-substituted amines:
- 4-methylbenzylamine to result in a chelator of formula (1a) wherein n is 1, x is 1 and R is methyl;
- 4-ethylbenzylamine to result in a chelator of formula (1a) wherein n is 1, x is 1 and R is ethyl;
- 4-isopropylbenzylamine to result in a chelator of formula (1a) wherein n is 1, x is 1 and R is isopropyl;
- 2,4,6-trimethylbenzylamine to result in a chelator of formula (1a) wherein n is 1, x is 3 and all R are methyl attached in the ortho-and para-positions;
- 3,5-dimethylbenzylamine to result in a chelator of formula (1a) wherein n is 1, x is 2 and all R are methyl in the meta-positions
- 4-phenylbenzylamine to result in a chelator of formula (1a) wherein n is 1, x is 1 and R is phenyl
- 4-fluorobenzylamine to result in a chelate of formula (1a) wherein n is 1, x is 1 and R is F
- phenylpropylamine to result in a chelator of formula (1a) wherein n is 3 and x is 0
- benzylamine to result in a chelator of formula (1a) wherein n is 1 and x is 0

Example 3

Preparation of gadolinium 1,4,7-tris(carbonylmethyl)-10-((4-tert-butyl)benzylaminocarbonylmethyl)-1,4,7,10-tetraazacyclo-dodecane, a Gd-chelate of formula (1)

1,4,7-Tris(carbonylmethyl)-10-(4-tert-butypbenzylaminocarbonylmethyl)-1,4,7,10-tetraazacyclododecane (1.10 g, 2 mmol) and $GdCl_3$-hexahydrate (0.74 g, 2 mmol) were dissolved in water (10 ml) at room temperature. The reaction mixture was heated to 90° C. and stirred for 2 h and the pH was continuously adjusted to 7 by addition of a 1 M aqueous NaOH. The reaction mixture was then cooled to room temperature and the pH was adjusted to 9 (aq. NaOH, 1M). The resulting opaque mixture was filtered and the pH was adjusted to 7 by addition of aq. HCl (1 M). The mixture was submitted to freeze-drying and the title compound was obtained as a white crystalline material.

In a similar way, other Gd-chelates of formula (1) were prepared starting from the following chelates of formula (1a)
- the chelator of formula (1a) wherein n is 1, x is 1 and R is methyl;
- the chelator of formula (1a) wherein n is 1, x is 1 and R is ethyl;
- the chelator of formula (1a) wherein n is 1, x is 1 and R is isopropyl;
- the chelator of formula (1a) wherein n is 1, x is 3 and all R are methyl attached in the ortho-and para-positions;
- the chelator of formula (1a) wherein n is 1, x is 2 and all R are methyl in the meta-positions
- the chelator of formula (1a) wherein n is 1, x is 1 and R is phenyl
- the chelator of formula (1a) wherein n is 1, x is 1 and R is F
- the chelator of formula (1a) wherein n is 3 and x is 0
- the chelator of formula (1a) wherein n is 1 and x is 0

Example 4

Production of a Solution of Hyperpolarised $^{13}C_1$-pyruvate Without the Presence of a Gd-chelate of Formula (1) (Comparison Example)

A composition being 15 mM in trityl radical of Example 1 was prepared by dissolving the trityl radical in $^{13}C_1$-pyruvic acid (164 µl). The composition was mixed to homogeneity, placed in a probe retaining container and inserted in the DNP polariser.

The composition was polarised under DNP conditions at 1.2 K in a 3.35 T magnetic field under irradiation with microwave (93.950 GHz). The solid state polarisation was monitored by $^{13}C$-NMR and polarisation was continued until a maximum of polarisation of 22% was obtained, i.e. a saturation curve was obtained in a graph showing NMR signal vs. time.

The solid composition comprising the hyperpolarised $^{13}C_1$-pyruvic acid was dissolved using a dissolution device according to WO-A-02/37132 in an aqueous solution of sodium hydroxide, tris(hydroxymethyl)aminomethane (TRIS) and ETDA (0.3 mM) to result in a neutral solution of hyperpolarised sodium $^{13}C_1$-pyruvate. In series with the dissolution device a chromatographic column was connected. The column consisted of a cartridge (D=38 mm; h=10 mm) containing hydrophobic packing material (Bondesil-C18, 40UM Part #:12213012) supplied by Varian. The solution was forced through the column which selectively adsorbed the trityl radical. The solution after filtration was analysed with a UV spectrophotometer at 469 nm and the residual trityl radical concentration was determined to be below the detection limit of 0.1 µM.

Example 5

Production of a Solution of Hyperpolarised $^{13}C_1$-pyruvate in the Presence of a Gd-Chelate of Formula (1)

A composition being 15 mM in trityl radical of Example 1, 1.5 mM in Gd-chelate of formula (1) and 3 mM in corresponding chelator of formula (1a) was prepared by dissolving the aforementioned compounds in $^{13}C_1$-pyruvic acid (164 µl). The composition was mixed to homogeneity, placed in a probe retaining container and inserted in the DNP polariser.

As Gd-chelates of formula (1) the following compounds were used:
Gd-chelate A: the Gd-chelate of formula (1) wherein n is 1, x is 1 and R is methyl;
Gd-chelate B: the Gd-chelate of formula (1) wherein n is 1, x is 1 and R is tert-butyl;
Gd-chelate C: the Gd-chelate of formula (1) wherein n is 3 and x is 0; and
Gd-chelate D: the Gd-chelate of formula (1) wherein n is 1 and x is 0

The corresponding chelators of formula (1a) were:
Chelator A: chelator of formula (1a) wherein n is 1, x is 1 and R is methyl;
Chelator B: chelator of formula (1a) wherein n is 1, x is 1 and R is tert-butyl;
Chelator C: chelator of formula (1a) wherein n is 3 and x is 0; and
Chelator D: chelator of formula (1a) wherein n is 1 and x is 0

DNP polarisation and measurement of the solid state polarisation were carried out as described in Example 4.

The maximum solid state polarisations obtained were measured to be the following for the compositions that contained
Gd-chelate A: 31% polarisation
Gd-chelate B: 29% polarisation
Gd-chelate C: 34% polarisation
Gd-chelate D: 34% polarisation Hence a polarisation enhancement of about 31-55% compared to the polarisation obtained in Example 4 could be achieved by adding the Gd-chelates of formula (1) to the composition to be polarised.

The solid compositions comprising the hyperpolarised $^{13}C_1$-pyruvic acid were dissolved using a dissolution device according to WO-A-02/37132 in an aqueous solution of sodium hydroxide and tris(hydroxymethyl)aminomethane (TRIS) and DTPAB-MA (1.5 mM) to result in a neutral solutions of hyperpolarised sodium $^{13}C_1$-pyruvate. In series with the dissolution device a chromatographic column was connected. The column consisted of a cartridge (D=38 mm; h=10 mm) containing hydrophobic packing material (Bondesil-C18, 40UM Part #:12213012) supplied by Varian. The solutions were forced through the column which selectively adsorbed the trityl radical, the Gd-chelates of formula (1) and the corresponding chelators. After filtration, the solutions were analysed with a UV spectrophotometer at 469 nm and the concentrations of residual trityl radical, Gd-chelates of formula (1) and corresponding chelators were determined. Said concentrations were found to be below the detection limit of 0.1 µM for trityl radical and 10 µM for Gd-chelate of formula (1) and corresponding chelators.

What is claimed is:
1. A compound of formula (1):

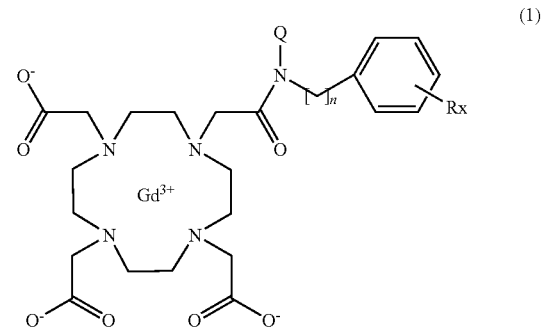

wherein
n is 1 to 10;
x is 0 to 3;
R is identical or different and represents fluoro, a straight chain or branched $C_1$-$C_6$-alkyl group or an aromatic or non-aromatic cyclic group containing 5 to 10 carbon atoms; and
Q is H, a straight chain or branched $C_1$-$C_6$-alkyl group, or an aromatic or non-aromatic cyclic group containing 5 to 10 carbon atoms or

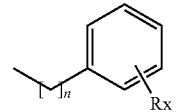

wherein n, x and R are as defined above.
2. The compound according to claim 1 wherein Q is H or

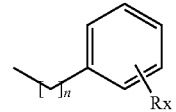

and R is identical or different and is fluoro, methyl, ethyl, propyl, isopropyl, butyl, iso-butyl, tert-butyl, cyclopentyl, cyclohexyl, methylcyclopentyl, methylcyclohexyl, benzyl, phenyl or tolyl.
3. The compound according to claims 1 wherein x is 1 and R is attached in the para-position.
4. The compound according to claim 1 wherein x is 0 and n is 1 to 5.
5. The compound according to claim 1 wherein x is 1 and R is attached in the para-position and is fluoro, methyl, isopropyl, isobutyl or tert-butyl.
6. The compound according to claim 1 wherein x is 0 and n is 1 to 3.
7. A composition comprising a carboxylic acid, a trityl radical and the compound of formula (1) according to claim 1.

8. The composition according to claim 7 wherein the carboxylic acid is $^{13}$C-enriched.

9. The composition according to claim 7 which further comprises a chelator and/or a Ca-chelate.

10. The composition according to claim 7 wherein the carboxylic acid is maleic acid, acetic acid, fumaric acid, pyruvic acid, malonic acid, succinic acid, oxaloacetic acid, lactic acid, α-ketoglutaric acid, nicotinic acid, alanine, glycine, cysteine, proline, tyrosine, sarcosine, GABA and homocysteine.

11. The composition according to claim 7 wherein the carboxylic acid is $^{15}$N and/or $^{13}$C-enriched.

12. The composition according to claim 7 wherein the trityl radical is a stable oxygen-based, sulfur-based or carbon-based trityl radical.

13. A composition comprising a hyperpolarised carboxylic acid or a salt thereof, a trityl radical, the compound of formula (1) according to claim 1.

14. The composition according to claim 13 which further comprises a chelator and/or a Ca-chelate.

15. A polarising agent comprising a trityl radical and the compound of formula (1) according to claim 1.

16. A method of producing a solid hyperpolarised carboxylic acid said method comprising:
preparing a composition comprising a carboxylic acid, a trityl radical and the compound of formula (1) according to claim 1;
cooling and/or freezing the composition; and
carrying out dynamic nuclear polarisation on the composition.

17. The method according to claim 16 wherein the solid hyperpolarised carboxylic acid is subsequently liquefied, either by dissolving the solid composition in an appropriate solvent or solvent mixture or by melting the solid composition, resulting in a liquid composition comprising the hyperpolarised carboxylic acid or a derivative thereof.

18. The method according to claim 16 wherein said composition further comprises a chelator and/or a Ca-chelate.

19. A method to produce the compound of formula (1) according to claim 1
by reacting
a) a DO3A derivative with protected carboxylic groups in a solvent and in the presence of a base with a compound of formula (3)

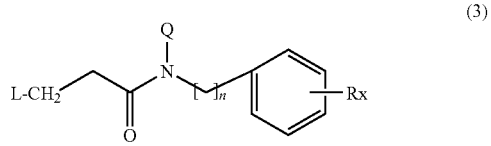

(3)

wherein L is a leaving group and Q, n, x and R are as defined in claim 1
b) removal of the protection groups; and
c) reacting the reaction product of step b) with a Gd$^{3+}$-compound in a solvent.

* * * * *